United States Patent [19]

Caransa et al.

[11] Patent Number: 4,914,029
[45] Date of Patent: Apr. 3, 1990

[54] PROCESS FOR STEEPING CEREALS WITH A NEW ENZYME PREPARATION

[75] Inventors: Abraham Caransa, Uithoorn, Netherlands; Timo Vaara; Martti Vaara, both of Helsinki, Finland; Maarit Simell, Vantaa, Finland; Antti Lehmussaari, Rajamaki, Finland

[73] Assignee: Dorr-Oliver Incorporated, Milford, Conn.

[21] Appl. No.: 242,243

[22] Filed: Sep. 12, 1988

[30] Foreign Application Priority Data

Nov. 17, 1987 [NL] Netherlands ............... 8702735

[51] Int. Cl.$^4$ .................. C12P 19/04; C12P 19/14
[52] U.S. Cl. ...................... 435/101; 435/99; 252/183.11
[58] Field of Search ................ 435/101, 99; 252/183.11

[56] References Cited

U.S. PATENT DOCUMENTS 4,596,776  6/1936  Nonaka et al. ............ 435/99
4,795,101  1/1989  Silver ..................... 241/21

OTHER PUBLICATIONS

M. Bartnik and I. Szafranska, *J. Cereal Sci.*, vol. 5; (1987), 23–28.
Ullah et al., *Preparative Biochemistry*, vol. 17(1), (1987), 63–91.
Ullah et al., *Preparative Biochemistry*, vol. 17(4), (1987), 397–422.
Shieh et al., *Applied Microbiology*, (Sep. 1968), 1348–1351.
F. G. Peers, *Biochem. J.*, vol. 53, (1953), 102–110.
Howson et al., *Enzyme Microb. Technol.*, vol. 5, (1983), 377–382.

*Primary Examiner*—Ronald W. Griffin
*Assistant Examiner*—Pamela S. Webber
*Attorney, Agent, or Firm*—Harold M. Snyder

[57] ABSTRACT

Corn or sorghum kernels are steeped in warm water containing sulfur dioxide in the presence of an enzyme preparation including one or more phytin-degrading enzymes, such as phytase and acid phosphatases, to eliminate or greatly reduce phytic acid and the salts of phytic acid.

26 Claims, No Drawings

PROCESS FOR STEEPING CEREALS WITH A NEW ENZYME PREPARATION

BACKGROUND OF THE INVENTION

The invention relates to a process for steeping corn or sorghum kernels in the production of starch and other products. As a matter of convenience only, the process will be described hereafter as applied to corn although equally applicable to sorghum.

Steeping of corn kernels is the first step in the processing of corn to obtain different product fractions like germs, proteins and starch. In this first step the hard corn kernels are steeped to soften them. The kernels absorb water and they swell. At the same time water-soluble substances are leached out of the corn and pass into the steepwater. The temperature of the steepwater is generally in the range 40°–55° C. The sulfur dioxide which is usually present in an amount of about 0.2%, by weight, breaks the cell wall structure and prevents the growth of microorganisms during steeping. The steeping process lasts about 48 hours. All subsequent steps, in which the different product fractions are obtained, are much shorter. The corn steep liquor (CSL) obtained is concentrated by evaporation. The product obtained will mainly be used as animal feed but is also utilized as a nutrient in microbial fermentations. The swollen kernels are further separated into germ, fiber, starch and protein fractions in succeeding steps.

As is common in many other plant seeds, phytic acid, the hexaphosphate ester of myoinositol, is present in the corn kernels. Phytic acid usually appears in the form of calcium and magnesium salts, which, as a class, are called phytin. A large part of the phosphorus present in plants is stored in these compounds. In the steeping process most of the phytic acid reports to the CSL. It forms an undesirable component therein for at least the reasons enumerated below:

(1) The phytic acid in CSL tends to deposit a sludge with
proteins and metal ions. This has caused problems in concentrating by evaporation and in transporting and storing the CSL.

(2) When used as a nutrient in microbial fermentations, CSL is diluted and the pH is raised to 4–5. When this medium is sterilized, the phytic acid forms a precipitate coating on the inner surface of the fermenter. This precipitate is hard to scrub off afterwards and it also interferes with the purification of the fermentation end products.

(3) When CSL is used as animal feed the phytic acid present gives the following problems. Phytic acid, because it interacts with multivalent metal ions, interferes with the assimilation of various metals in the body of animals (and humans). This may lead to deficiency disorders. Phytic acid also inhibits the activity of various enzymes in the body such as pepsin. Besides, the phosphate present in the phytic acid is not available for monogastric animals, because they only can digest phytic acid to a restricted extent.

There have been proposals for removing phytic acid from the CSL. Thus, U.S. Pat. No. 2,515,157 describes a process for the treatment of CSL to obtain an improved nutrient for antibiotic fermentations. In this process the phytic acid is removed by adding an aluminum ion-furnishing compound to the CSL at low pH, heating and separating the aluminum phytate formed.

U.S. Pat. No. 2,712,516 describes a similar process wherein phytate is precipitated as its calcium salt.

The processes described in the above-mentioned U.S. patents are performed following the steeping process. Therefore, an additional step is required for removing phytic acid.

SUMMARY OF THE INVENTION

It has now been found that the additional step specified in the prior art can be avoided by performing the steeping in the presence of an enzyme preparation comprising one or more phytin-degrading enzymes.

Broadly speaking, the process of the invention calls for steeping corn or sorghum kernels in warm water containing sulfur dioxide in the presence of an enzyme preparation comprising one or more phytin-degrading enzymes.

In more detail, this invention provides a process for processing corn or sorghum, which comprises the consecutive steps of
 (a) steeping corn or sorghum kernels in warm water containing sulfur dioxide in the presence of an enzyme preparation comprising one or more phytin-degrading enzymes,
 (b) separating the steepwater from the kernels and concentrating it,
 (c) milling the kernels coarsely and separating and dewatering germs,
 (d) fine-milling the kernels, separating fibers from starch and protein, and dewatering the fiber fraction, and
 (e) separating starch and protein from each other, concentrating the protein fraction and drying and/or converting the starch fraction.

Preferably the enzyme preparation comprises such an amount of one or more phytin-degrading enzymes that the phytin present in the kernels is substantially degraded. The term "phytin" as used herein embraces the salts of phytic acid and also phytic acid itself.

Phytin degrading enzymes dephosphorylate inositol phosphates to yield inositol and orthophosphate. Phytin-degrading enzymes include phytase and acid phosphatases. Phytase and acid phosphatases are produced by various microorganisms like Aspergillus spp., Rhizopus spp. and yeasts (Appl. Microbial 16 (1968) 1348–1357; Enzyme Microb. Technol. 5 (1983), 377–382) while phytase is also produced by various plant seeds, as for example wheat, during germination. Phytin-degrading enzymes are very active at the low pH of the steepwater. According to methods known in the art, enzyme preparations can be obtained from the above mentioned organisms. It is found that phytin in corn is degraded most efficiently with enzymes from Aspergillus spp. Thus, at the same enzyme dosage an *Aspergillus niger* enzyme preparation is more efficient than wheat phytase.

Microbially produced enzyme preparations may comprise additional plant material degrading enzymes such as enzymes having cellulase, hemicellulase and/or pectinase activity. These other activities contribute to the advantages which are obtained by the process of the invention. Suitable enzyme preparations are for example enzymes of the Econase EP 43 series manufactured by Alko Ltd.

The temperature during the steeping process according to the invention is maintained in the range 20°–60°

C., and generally about 50° C. The applied amount of enzyme preparation depends on the preparation used, the phytin contents of the corn kernels and the reaction conditions. The right dosage can easily be estimated by a person skilled in the art.

The process according to the invention offers, besides avoiding an additional step, various important advantages. First, by adding the enzyme preparation the steeping process is accelerated to such an extent that the steeping time may be reduced considerably. Since the steeping process is the longest step in total corn processing, a reduction thereof is of great economical importance. Thus the steeping process may be reduced to only 12 hours without any losses in the main product fraction yields. Preferably steeping time will be 12–18 hours; however, longer steeping times up to 48 hours are possible.

Secondly, the separation processes after the steeping process according to the invention are improved and give higher yields. When steeping is performed for 16 hours, for example, in the presence of the enzyme preparation, the yield of starch is higher than in the case of the conventional steeping process.

Thirdly, steeping corn in the presence of phytin-degrading enzymes leads to corn steep liquor that does not contain phytin. As a result, concentration of CSL is easier and the product obtained is excellently suitable for animal feed and for microbial fermentations.

The steeping time can yet be further reduced by performing the steeping process in two steps, first steeping for 4–10 hours, followed by milling the corn kernels and then further steeping the milled corn kernels for another 3–6 hours. Preferably the second stage of this double stage steeping is carried out in water not containing sulfur dioxide.

DETAILED DESCRIPTION OF THE INVENTION

In the examples which follow, the process of the invention is carried out on laboratory scale by standard Pelshenke and Lindemann determination. As may be expected, the results obtained when carrying out the process industrially will be similar or even better due to improved separating techniques.

EXAMPLE I

In a number of tests 50 g of corn kernels are steeped in water of 50° C. containing 0.2% by weight, sulfur dioxide, in the presence or in the absence of an amount of Econase EP 434. This enzyme preparation has as major activities phytin and cellulose degrading activities and as minor activities hemicellulase and pectinase. The steeping times of the tests vary from 12 to 48 hours, as shown in Table A.

The enzyme dosages are presented as phytin-degrading units/g of corn. One phytin-degrading unit (1 PU) is the amount of enzyme which liberates 1 nmol (nano mol) of inorganic phosphorus from sodium phytate per minute under standard conditions (40° C., pH 5.5). The kernels after steeping are processed further to obtain the product fractions mentioned in Table B.

TABLE A

| Test | 1 | 2 | 3 | 4 | 5 | 6 |
|---|---|---|---|---|---|---|
| steeping time (h) | 48 | 48 | 24 | 20 | 16 | 12 |
| dosage of Econase EP 434 (PU/g corn) | — | 70 | 135 | 160 | 200 | 270 |

TABLE B

| | Results of single stage steeping | | | | | |
|---|---|---|---|---|---|---|
| | Yield in % of dry weight | | | | | |
| Test | 1 | 2 | 3 | 4 | 5 | 6 |
| dry substance in CSL | 5.28 | 5.61 | 4.78 | 4.72 | 4.23 | 3.91 |
| germs | 7.34 | 7.12 | 7.42 | 7.66 | 9.00 | 7.51 |
| fibers (starch content)[a] | 9.70 | 9.21 | 9.55 | 9.52 | 9.41 | 9.70 |
| | (19.01) | (17.16) | (16.91) | (8.60) | (16.71) | (17.46) |
| starch (protein content)[a] | 64.09 | 65.49 | 65.29 | 65.38 | 66.20 | 64.00 |
| | (0.37) | (0.37) | (0.35) | (0.43) | (0.39) | (0.44) |
| gluten (protein content)[a] | 7.31 | 6.24 | 7.57 | 8.12 | 6.94 | 9.42 |
| | (46.57) | (51.43) | (47.52) | (49.21) | (57.60) | (42.76) |
| dry substance in supernatant | 2.21 | 2.25 | 2.88 | 2.89 | 3.00 | 2.59 |
| starch recovery | 94.4 | 96.5 | 96.2 | 96.3 | 97.5 | 94.3 |
| total dry substance recovery | 95.91 | 95.92 | 97.49 | 98.29 | 98.78 | 97.15 |

[a]expressed as % of the fraction

It appears from Table B that the starch yield after 16 to 48 hours of single stage steeping in the presence of the enzyme preparation is higher than in the case of conventional steeping without enzyme preparation, and after 12 hours of steeping in the presence of the enzyme preparation the starch yield is almost as high as in the case of conventional steeping without enzyme preparation.

EXAMPLE II 50 g of corn kernels are presteeped in water of 50° C. containing 0.2%, by weight, sulfur dioxide and Econase EP 434 providing 135 PU/g of corn for 6 hours. Following manual degermination, the product is milled coarsely. Then the germs are added back to the slurry. Thereafter, the second stage of the steeping is carried out in fresh water of 50° C. containing Econase EP 434 providing 135 PU/g of corn for 4 hours. The suspension obtained is processed further to obtain the product fractions mentioned in Table C.

TABLE C

| | Yield in % of dry weight |
|---|---|
| dry substance in CSL | 2.19 |
| germs | 8.80 |
| fibers (starch content) | 9.64 (20.99) |
| starch (protein content) | 65.53 (0.37) |
| gluten (protein content) | 6.8 (56.74) |
| dry substance in supernatant | 5.45 |
| starch recovery | 96.5 |
| total dry substance recovery | 98.41 |

Note: In this test it is necessary to degerminate before milling because the mill used would damage the germ. When the double stage steeping is carried out industrially, a mill would be used which will not damage the germ. Degermination is not necessary then.

Examples I and II demonstrate that in using the process of the invention there is essentially no sacrifice in star production despite the shorter steeping times utilized.

EXAMPLE III

CSL is diluted 1:10 and the pH is adjusted to 5.0. Corn flour is diluted 1:10 with 0.2 M citrate buffer pH 5.0. Sodium azide is added at a concentration of 0.02%, by weight, to inhibit microbial growth. Aspergillus spp. enzyme preparation containing phytin degrading activity or wheat phytase (Sigma P-1259) is added at a dosage of 7000 PU/gram of phytin (300 PU per each ml of CSL dilution and 150 PU per each 2 grams of corn flour).

Suspensions are incubated in a shaker (250 rpm) at 50° C. At fixed intervals the reaction is stopped with equal volume of 6% (w/v) $H_2SO_4$. Phytate is extracted to the acidic liquid for 30 min. at room temperature. Phytic acid is then precipitated from a clear supernatant with ferric chloride. Ferric ions are removed by precipitation with sodium hydroxide. Phytate is determined by HPLC (High Performance Liquid Chromatography) using sodium phytate as a standard.

Table D shows the residual phytin content of CSL and corn flour after incubation with phytin-degrading enzymes. In experiment (a) incubation is carried out with Aspergillus spp. enzyme preparation, and in experiment b) incubation is carried out with wheat phytase.

TABLE D

Comparing Aspergillus spp. enzyme preparation and wheat phytase.

| Substrate | Incubation time (h) | Phytin (as phytic acid) | | | |
|---|---|---|---|---|---|
| | | exp. (a) | | exp. (b) | |
| | | mg/ml | % | mg/ml | % |
| CSL | 0 | 3.1 | 100 | 3.4 | 100 |
| | 2 | 2.7 | 87 | 2.4 | 71 |
| | 4 | 1.4 | 45 | 1.9 | 56 |
| | 10 | 1.0 | 32 | 2.0 | 59 |
| | 24 | 0 | 0 | 1.4 | 41 |
| corn flour | 0 | 13.6 | 100 | 11.4 | 100 |
| | 2 | 9.1 | 67 | 9.1 | 80 |
| | 4 | 0 | 0 | 7.9 | 69 |
| | 10 | 0 | 0 | 6.8 | 60 |
| | 24 | 0 | 0 | 2.3 | 20 |

Table D shows that phytic acid content can be reduced considerably with both phytin degrading enzymes. At the same enzyme dosage Aspergillus spp. enzyme preparation is more efficient than wheat phytase.

EXAMPLE IV 25 g of corn kernels are steeped in 50 ml water of 50° C. containing 0.2%, by weight, sulfur dioxide. In the control no enzyme preparation is added and in the test according to the invention, an Aspergillus spp. enzyme preparation is added at a dosage of 135 PU/g corn. Steeping time is 24 hours or 48 hours.

After steeping, an amount of CSL is extracted for 30 min. with an equal volume of 6% (w/v) $H_2SO_4$ at room temperature. Phytic acid is precipitated from a clear supernatant with ferric chloride. Ferric ions are removed by precipitation with sodium hydroxide. Phytate is determined by HPLC using sodium phytate as a standard.

Table E shows the amount of phytic acid in CSL. Experiment (a) comprises conventional steeping without phytin-degrading enzymes and experiment b) comprises steeping in the presence of the above enzyme preparation.

TABLE E

| | Phytin content of CSL | |
|---|---|---|
| | mg phytic acid/ml CSL | |
| steeping time (h) | exp. (a) | exp. (b) |
| 24 | 1.6 | 0 |
| 48 | 3.1 | 0 |

Table E shows that when corn kernels are steeped in the presence of phytin degrading enzymes CSL is free from phytin.

EXAMPLE V

Econase EP 434 and a plant cell wall degrading enzyme preparation with negligible phytin-degrading activity are tested in one-step and in two-step steeping.

In one-step steeping 50 g of corn kernels are steeped in water of 50° C. containing 0.2%, by weight, sulfur dioxide. The dosage of Econase EP 434 is 135 PU/g corn. Equal volume of the plant cell wall degrading enzyme preparation with negligible phytin-degrading activity is applied. Steeping time is 20 hours. The kernels are processed further according to Pelshenke and Lindemann method.

In two-step steeping, 50 g of corn kernels are pre-steeped for 6 hours in water of 50° C. containing 0.2%, by weight, sulfur dioxide and Econase EP 434 providing 135 PU/g corn or an equal volume of plant cell wall degrading enzyme preparation with negligible phytin-degrading activity. Following manual degermination, the product is milled coarsely. Then the germs are added back to the slurry. Thereafter, the second stage of the steeping is carried out for 4 hours in fresh water of 50° C. containing Econase EP 434 providing 135 PU/g corn or an equal volume of plant cell wall degrading enzyme preparation with negligible phytin-degrading activity. The slurry is further processed according to Pelshenke and Lindemann method.

The test results obtained are shown in the following Table F.

TABLE F

Starch recoveries with different enzyme preparations.
1. Econase EP 434
2. plant cell wall degrading enzyme preparation with negligible phytin degrading activity.

| Steeping process | Steeping time h | enzyme | starch recovery % |
|---|---|---|---|
| One-step | 20 | 1 | 97.0 |
| | 20 | 2 | 94.4 |
| Two-step | 6 + 4 | 1 | 96.5 |
| | 6 + 4 | 2 | 91.4 |

It appears from Table F that the starch yield is higher when the kernels are treated with an enzyme preparation containing phytin-degrading activity.

There has thus been provided a remarkably simple process for steeping cereals to substantially degrade the deleterious phytin present in the cereal kernels without loss of starch product.

Although the present invention has been described in conjunction with preferred process embodiments, it is to be understood that modifications and variations in the process may be resorted to without departing from the spirit and scope of the invention, as those skilled in the art will readily understand. Such modifications and variations are considered to be within the purview and scope of the invention and appended claims.

We claim:

1. A steeping process for corn or sorghum kernels capable of yielding an essentially phytin-free steep liquor wherein said kernels are steeped in warm water or process water containing sulfur dioxide in the presence of an enzyme preparation comprising at least one phytin-degrading enzyme in an amount capable of degrading the phytin in said kernels.

2. The process according to claim 1, wherein at least one phytin-degrading enzyme is selected from a group consisting of phytases or acid phosphatases.

3. The process according to claim 1, wherein the phytin-degrading enzymes are used in the presence of other plant material degrading enzymes.

4. The process according to claim 3, wherein said other plant material degrading enzymes are selected from a group consisting of cellulase, hemicellulase and pectinase activities.

5. The process according to claim 1, wherein the phytin-degrading enzymes are prepared from plant or microbial sources capable of producing phytin-degrading enzymes.

6. The process according to claim 5, wherein the plant source containing phytin-degrading enzymes is wheat.

7. The process according to claim 1, wherein said phytin-degrading enzyme is derived from an Aspergillus spp. strain capable of producing phytin-degrading enzymes.

8. The process according to claim 1 wherein the corn and sorghum kernels are steeped for 12–48 hours when the temperature of the water is 20°–60° C.

9. The process according to claim 8 wherein the kernels are steeped for 12–18 hours.

10. An essentially phytin-free steep liquor prepared in accordance with the steeping process of claims 1, 2, 4 or 8.

11. A process for the production of starch and protein by processing corn or sorghum, which comprises the consecutive steps of:
(a) steeping corn or sorghum kernels in warm water or process water containing sulphur dioxide in the presence of an enzyme preparation comprising phytin degrading enzymes;
(b) separating the steepwater from the kernels and concentrating it;
(c) milling the kernels coarsely and separating and dewatering germs;
(d) fine-milling the kernels, separating fibers from starch and protein, and dewatering the fiber fractions, and
(e) separating starch and protein from each other.

12. A process according to claim 11, wherein the steeping step is performed in two steps, first steeping for 4–10 hours followed by milling the kernels and then further steeping the milled kernels for another 3–6 hours.

13. A process according to claim 12, wherein the second stage of the steeping is carried out in water wherein sulfur dioxide is not present.

14. The process according to claim 11, wherein the preparation comprises phytin-degrading enzyme, in amounts capable of degrading the phytin.

15. The process according to claim 11, wherein the phytin-degrading enzymes are selected from a group consisting of phytase or acid phosphatase.

16. The process according to claim 11, wherein phytin-degrading enzymes are used in the presence of other plant material degrading enzymes.

17. The process according to claim 16, wherein the other plant material degrading enzymes are selected from a group consisting of cellulase, hemicellulase and pectinase activities.

18. The process according to claim 11, wherein the phytin-degrading enzymes are prepared from plant or microbial sources capable of producing phytin-degrading enzymes.

19. The process according to claim 18, wherein the plant source containing phytin-degrading enzymes is wheat.

20. The process according to claim 18, wherein the phytin-degrading enzymes are derived from an Aspergillus spp. strain capable of producing phytin-degrading enzymes.

21. The process according to claim 11 wherein the corn and sorghum kernels are steeped for 12–48 hours when the temperature of the water is 20°–60° C.

22. The process according to claim 21 wherein the kernels are steeped for 12–18 hours.

23. An aqueous steeping liquor for cereals comprising water, sulfur dioxide and a phytin-degrading enzyme component.

24. The steeping liquor of claim 23 wherein the phytin-degrading enzyme component is selected from the group consisting of phytases and acid phosphatases.

25. The steeping liquor of claim 23 wherein the temperature of the water is 20°–60° C.

26. The steeping liquor as in claims 23, 24, or 25 which further includes plant material degrading enzymes selected from the group consisting of cellulase, hemicellulase and pectinase activities.

* * * * *

UNITED STATES PATENT AND TRADEMARK OFFICE
CERTIFICATE OF CORRECTION

PATENT NO. : 4,914,029

DATED : April 3, 1990

INVENTOR(S) : Abraham Caransa, Timo Vaara, Martti Vaara, Maarit Simell, Antti Lehmussaari It is certified that error appears in the above-identified patent and that said Letters Patent is hereby corrected as shown below:

On the title page item, [73], correct the text to read:

--[73] Assignees: Dorr-Oliver Incorporated, Milford, CT
and
Alko Ltd., Helsinki, Finland--

Signed and Sealed this

Second Day of July, 1991

Attest:

HARRY F. MANBECK, JR.

Attesting Officer

Commissioner of Patents and Trademarks